US00PP29011P2

(12) United States Plant Patent
van Sambeek

(10) Patent No.: US PP29,011 P2
(45) Date of Patent: Feb. 27, 2018

(54) ***LEUCANTHEMUM* PLANT NAMED 'BARLEUSWECHR'**

(50) Latin Name: *Leucanthemum×superbum*
Varietal Denomination: Barleuswechr

(71) Applicant: Ellen van Sambeek, Aalsmeer (NL)

(72) Inventor: Ellen van Sambeek, Aalsmeer (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/330,236

(22) Filed: Aug. 27, 2016

(51) Int. Cl.
*A01H 5/02* (2006.01)

(52) U.S. Cl.
USPC ..... Plt./285

(58) Field of Classification Search
USPC ..... Plt./285
See application file for complete search history.

*Primary Examiner* — Anne M Grunberg
(74) *Attorney, Agent, or Firm* — C. A. Whealy

(57) ABSTRACT

A new and distinct cultivar of *Leucanthemum* plant named 'Barleuswechr', characterized by its compact, upright and mounded plant habit; freely branching habit; strong and upright flowering stems; early and freely flowering habit; and large single inflorescences with white-colored ray florets.

1 Drawing Sheet

Botanical designation: *Leucanthemum×superbum.*
Cultivar denomination: 'BARLEUSWECHR'.

BACKGROUND OF THE INVENTION

The present invention relates to a new and distinct cultivar of *Leucanthemum* plant, botanically known as *Leucanthemum×superbum* and hereinafter referred to by the name 'Barleuswechr'.

The new *Leucanthemum* plant is a product of a planned breeding program conducted by the Inventor in Aalsmeer, The Netherlands. The objective of the breeding program is to create new compact *Leucanthemum* plants with numerous attractive inflorescences.

The new *Leucanthemum* plant originated from a cross-pollination in June, 2013 of a proprietary selection of *Leucanthemum×superbum* identified as code number LC-0008, not patented, as the female, or seed, parent with a proprietary selection of *Leucanthemum×superbum* identified as code number LC-0003, not patented, as the male, or pollen, parent. The new *Leucanthemum* plant was discovered and selected by the Inventor as a single flowering plant from within the progeny of the stated cross-pollination in a controlled environment in Aalsmeer, The Netherlands in February, 2014.

Asexual reproduction of the new *Leucanthemum* plant by vegetative terminal cuttings in Aalsmeer, The Netherlands, since March, 2014 has shown that the unique features of this new *Leucanthemum* plant are stable and reproduced true to type in successive generations.

SUMMARY OF THE INVENTION

Plants of the new *Leucanthemum* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Barleuswechr'. These characteristics in combination distinguish 'Barleuswechr' as a new and distinct *Leucanthemum* plant:

1. Compact, upright and mounded plant habit.
2. Freely branching habit.
3. Strong and upright flowering stems.
4. Early and freely flowering habit.
5. Large single inflorescences with white-colored ray florets.

Plants of the new *Leucanthemum* differ primarily from plants of the female parent selection in the following characteristics:

1. Plants of the new *Leucanthemum* are more freely branching than plants of the female parent selection.
2. Plants of the new *Leucanthemum* are more freely flowering than plants of the female parent selection.
3. Inflorescences of plants of the new *Leucanthemum* have fewer ray florets than inflorescences of plants of the female parent selection.

Plants of the new *Leucanthemum* differ primarily from plants of the male parent selection in the following characteristics:

1. Plants of the new *Leucanthemum* are more compact than plants of the male parent selection.
2. Plants of the new *Leucanthemum* are more freely branching than plants of the male parent selection.
3. Plants of the new *Leucanthemum* have larger inflorescences than plants of the male parent selection.

Plants of the new *Leucanthemum* can be compared to plants of *Leucanthemum×superbum* 'Victorian Secret', disclosed in U.S. Plant Pat. No. 22,654. In side-by-side comparisons, plants of the new *Leucanthemum* differ from plants of 'Victorian Secret' in the following characteristics:

1. Plants of the new *Leucanthemum* are shorter than plants of 'Victorian Secret'.
2. Plants of the new *Leucanthemum* are more freely branching than plants of 'Victorian Secret'.

3. Plants of the new *Leucanthemum* are more freely flowering than plants of 'Victorian Secret'.
4. Inflorescences of plants of the new *Leucanthemum* have fewer ray florets than inflorescences of plants of 'Victorian Secret'.
5. Inflorescences of plants of the new *Leucanthemum* have more disc florets than inflorescences of plants of 'Victorian Secret'.

BRIEF DESCRIPTION OF THE PHOTOGRAPH

The accompanying colored photograph illustrates the overall appearance of the new *Leucanthemum* plant showing the colors as true as it is reasonably possible to obtain in colored reproductions of this type. Colors in the photograph may differ slightly from the color values cited in the detailed botanical description which accurately describe the colors of the new *Leucanthemum* plant.

The photograph is a side perspective view of a typical flowering plant of 'Barleuswechr' grown in a container.

DETAILED BOTANICAL DESCRIPTION

The aforementioned photograph and following observations and measurements describe plants grown in 13-cm containers during the early summer in a glass-covered greenhouse in Aalsmeer, The Netherlands and under cultural practices typical of commercial *Leucanthemum* production. During the production of the plants, day temperatures averaged 21° C. and night temperatures averaged 16° C. Plants were pinched one time and were three months old when the photograph and four months old when the description were taken. In the following description, color references are made to The Royal Horticultural Society Colour Chart, 2007 Edition, except where general terms of ordinary dictionary significance are used.

Botanical classification: *Leucanthemum×superbum* 'Barleuswechr'.

Parentage:

*Female, or seed, parent*.—Proprietary selection of *Leucanthemum×superbum* identified as code number LC-0008, not patented.

*Male, or pollen, parent*.—Proprietary selection of *Leucanthemum×superbum* identified as code number LC-0003, not patented.

Propagation:

*Type*.—Terminal vegetative cuttings.

*Time to initiate roots, summer*.—About twelve days at temperatures about 26° C.

*Time to initiate roots, winter*.—About two weeks at temperatures about 23° C.

*Time to produce a rooted young plant, summer*.—About two weeks at temperatures about 23° C.

*Time to produce a rooted young plant, winter*.—About 16 days at temperatures about 18° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately freely branching, medium density.

Plant description:

*Plant and growth habit*.—Herbaceous perennial; compact, upright and mounded plant habit; vigorous growth habit; freely branching habit with about 15 to 20 primary branches each with about three secondary branches developing per plant.

*Plant height*.—About 35 cm.

*Plant width*.—About 45 cm.

*Branch description*.—Length: About 35 cm. Diameter: About 1.5 mm. Internode length: About 2 cm. Strength: Strong. Texture: Sparsely pubescent. Luster: Semi-glossy. Color: Close to 145A.

*Leaf description*.—Arrangement: Alternate; simple; occasionally sessile. Length: About 15 cm. Width: About 3.5 cm. Shape: Roughly spatulate. Apex: Obtuse. Base: Attenuate. Margin: Serrate. Texture and luster, upper surface: Pubescent; matte. Texture and luster, lower surface: Smooth, glabrous; matte. Venation pattern: Prominent midvein; reticulate. Color: Developing leaves, upper surface: Close to 137A. Developing leaves, lower surface: Close to 137C. Fully developed leaves, upper surface: Close to 137A; venation, close to 145B. Fully developed leaves, lower surface: Close to 137C; venation, close to 145B. Petioles: Length: About 9 cm. Diameter: About 5 mm. Texture and luster, upper and lower surfaces: Smooth, glabrous; matte. Color, upper and lower surfaces: Close to 145B.

Inflorescence description:

*Appearance*.—Single inflorescence form with recurving ray florets and tubular disc florets; inflorescences held upright on strong peduncles, inflorescences face mostly upright; ray and disc florets develop acropetally on a capitulum.

*Fragrance*.—None detected.

*Flowering response*.—Plants begin flowering about twelve weeks after planting; plants flower naturally during June and July in The Netherlands.

*Postproduction longevity*.—Inflorescences maintain good substance for about six to eight weeks on the plant; inflorescences persistent.

*Quantity of inflorescences*.—Freely flowering habit, about 52 inflorescences develop per plant during the flowering season.

*Inflorescence size*.—Diameter: About 15 cm. Depth (height): About 3.5 cm. Disc diameter: About 2.5 cm.

*Receptacles*.—Height: About 1 cm. Diameter: About 2.5 cm. Color: Close to 6A.

*Inflorescence buds*.—Height: About 8mm. Diameter: About 1.4 cm. Shape: Flattened sphere. Color: Close to 138B.

*Ray florets*.—Quantity per inflorescence: About 46 arranged in about two whorls. Length: About 3.3 cm. Width: About 6 mm. Shape: Ligulate to oblanceolate. Apex: Emarginate. Base: Attenuate. Margin: Entire. Aspect: Horizontal to recurved. Texture and luster, upper and lower surfaces: Smooth, glabrous; matte. Color: When opening, upper and lower surfaces: Close to 155D; towards the base, close to 144B. Fully opened, upper and lower surfaces: Close to 155D; towards the base, close to 144B; color does not change with development.

*Disc florets*.—Quantity per inflorescence: About 350 massed at the center of the receptacle. Length: About 7 mm. Diameter: About 1 mm. Shape: Short, fused tubular. Apex: Acute, five-pointed. Texture and luster, inner and outer surfaces: Smooth, glabrous; lustrous. Color: When opening, inner surface: Close to 144A. When opening, outer surface: Close to 14A.

Fully opened, inner surface: Close to 14A; color does not change with development. Fully opened, outer surface: Close to 14A; color becoming close to 144A with development.

*Involucral bracts*.—Quantity per inflorescence: About 40 arranged in about three whorls. Length: About 9 mm. Width: About 3 mm. Shape: Ovate. Apex: Obtuse. Base: Fused, truncate. Margin: Entire, membraneous. Texture and luster, upper and lower surfaces: Smooth, glabrous; lustrous. Color, upper and lower surfaces: Close to 137B.

*Peduncles*.—Length: About 19 cm. Diameter: About 3 mm. Strength: Strong. Aspect: Upright to about 30° from vertical. Texture and luster: Pubescent; matte. Color: Close to 137D.

*Reproductive organs*.—Androecium: Present on disc florets only. Quantity per floret: Five per disc floret. Filament length: About 2 mm. Filament color: Close to 14A. Anther shape: Oblong. Anther color: Close to 23A. Pollen amount: Abundant. Pollen color: Close to 23A. Gynoecium: Present on ray and disc florets. Quantity per floret: One. Pistil length: About 4 mm. Stigma shape: Bi-parted. Stigma diameter: Close to 1 mm. Stigma color: Close to 10C. Style length: About 3 mm. Style color: Close to 2D. Ovary color: Close to 143C.

*Seeds and fruits*.—Seed and fruit production have not been observed on plants of the new *Leucanthemum*.

Disease & pest resistance: Plants of the new *Leucanthemum* have not been observed to be resistant to pathogens and pests common to *Leucanthemum* plants.

Garden performance: Plants of the new *Leucanthemum* have been observed to have good garden performance and to tolerate wind and rain, to tolerate temperatures ranging from −15° C. to 35° C.

It is claimed:

1. A new and distinct *Leucanthemum* plant named 'Barleuswechr' as illustrated and described.

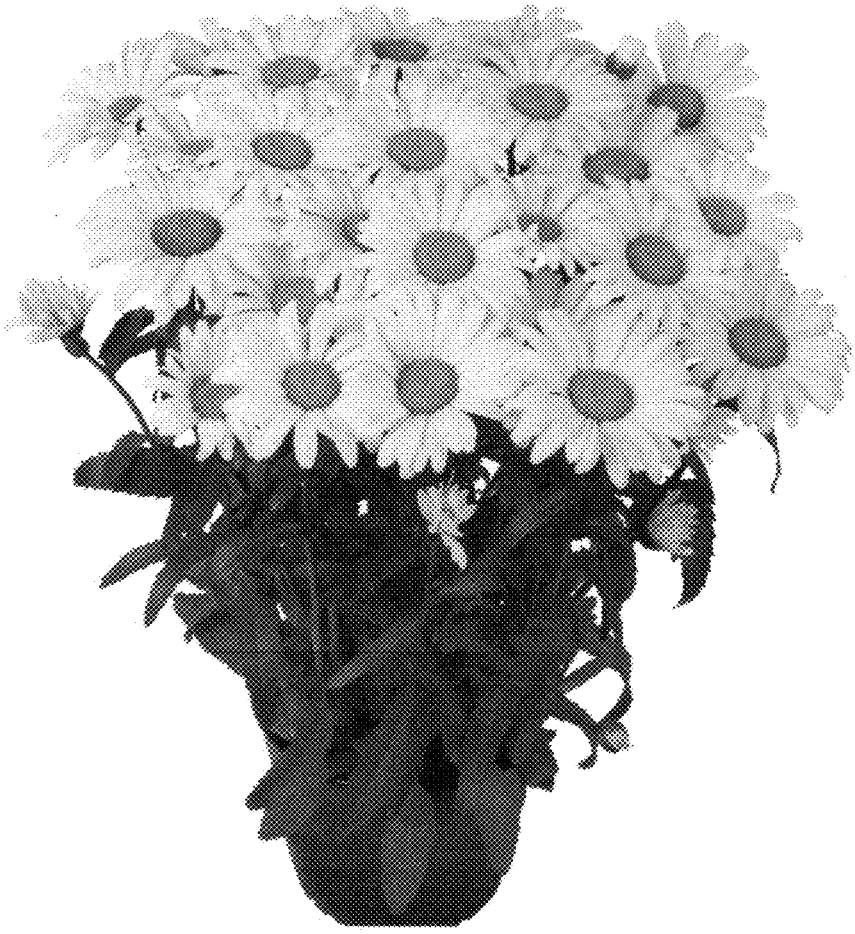

* * * * *